(12) United States Patent
Anderson et al.

(10) Patent No.: US 12,295,569 B1
(45) Date of Patent: May 13, 2025

(54) MULTIPLE PASS SELF-CINCHING SUTURE CONSTRUCT

(71) Applicant: INS Ortho, Inc., Providence, RI (US)

(72) Inventors: Christian N. Anderson, Nashville, TN (US); Samuel Grossman, Barrington, RI (US)

(73) Assignee: INS Ortho, Inc., Providence, RI (US)

( * ) Notice: Subject to any disclaimer, the term of this patent is extended or adjusted under 35 U.S.C. 154(b) by 0 days.

(21) Appl. No.: 18/946,857

(22) Filed: Nov. 13, 2024

Related U.S. Application Data

(60) Provisional application No. 63/642,207, filed on May 3, 2024.

(51) Int. Cl.
*A61B 17/06* (2006.01)
*A61B 17/04* (2006.01)

(52) U.S. Cl.
CPC .......... *A61B 17/06166* (2013.01); *A61B 2017/0496* (2013.01)

(58) Field of Classification Search
CPC .......... A61B 17/06166; A61B 2017/0496
See application file for complete search history.

(56) References Cited

U.S. PATENT DOCUMENTS

| | | | | |
|---|---|---|---|---|
| 12,096,928 | B2* | 9/2024 | Kaiser | A61B 17/0487 |
| 2018/0021036 | A1* | 1/2018 | Kaiser | A61B 17/06166 606/232 |
| 2024/0081807 | A1* | 3/2024 | Stone | A61B 17/0469 |
| 2024/0277334 | A1* | 8/2024 | Anderson | A61B 17/0401 |

* cited by examiner

*Primary Examiner* — Phong Son H Dang
(74) *Attorney, Agent, or Firm* — Holland & Knight LLP; Matthew C. Cox

(57) ABSTRACT

A multiple pass self-cinching suture construct includes a strand of suture material. A fixed loop is formed at one end, and an adjustable loop is formed at the opposite end. A self-cinching section is disposed between the fixed loop and the adjustable loop. The self-cinching section includes a first pass of a tag end axially through the interior of the self-cinching section to form the fixed loop. The opposite tag end passes axially through the interior of two co-axial suture segments inside the self-cinching section, forming an adjustable loop. As the adjustable loop tag end is pulled, tension is applied and the self-cinching section constricts to maintain tension. In some embodiments, the self-cinching section includes at least four segments of the strand of suture material co-axially aligned along the self-cinching section.

20 Claims, 18 Drawing Sheets

MULTIPLE PASS SELF-CINCHING SUTURE CONSTRUCT

CROSS-REFERENCES TO RELATED APPLICATIONS

This patent application is a non-provisional of, and claims benefit of and priority to, U.S. Provisional Patent Application No. 63/642,207 filed May 3, 2024, all of which is hereby incorporated by reference in its entirety.

STATEMENT REGARDING FEDERALLY SPONSORED RESEARCH OR DEVELOPMENT

Not applicable.

REFERENCE TO SEQUENCE LISTING OR COMPUTER PROGRAM LISTING INDEX

Not applicable.

TECHNICAL FIELD

The present disclosure relates to devices and methods for orthopedic surgery, and more particularly to suture construct devices and methods.

BACKGROUND

Conventional suture constructs for use in orthopedic surgery include one or more strands of suture material that may be fixed to tissue, bone or ligaments and tightened to approximate anatomical positioning and to promote healing. Conventional suture constructs must be tightened using knots or anchors to maintain tension during recovery. However, knots applied to conventional suture constructs may loosen over time, thereby reducing the effectiveness of the suture construct and leading to post-surgical complications and undesirable outcomes.

To overcome the problems associated with conventional knotted suture constructs, others have developed knotless suture constructs that rely on mechanical self-cinching constriction of co-axially or transversely aligned suture strands. However, conventional knotless self-cinching suture constructs may slip during cyclic loading, leading to loosening of the construct and undesirable outcomes.

What is needed then, are improvements in devices and methods for suture constructs for repairing and reconstructing tissue in orthopedic surgical procedures.

BRIEF SUMMARY

The present disclosure provides improved knotless self-cinching suture constructs and associated methods for orthopedic surgery.

A suture construct including an adjustable loop at a first end, a fixed loop at a second end, and a self-cinching section disposed between the adjustable and fixed loops is provided. The self-cinching section includes multiple overlapping co-axial segments of a single suture strand housed inside the self-cinching section in some embodiments to enhance mechanical constriction of the suture construct during tensioning.

In some embodiments, a suture construct includes a multiple pass configuration wherein a self-cinching sleeve is first formed using a tag end of a suture strand spliced axially through itself. The other tag end of the same suture strand (including the opposite tag end axially housed within the suture strand) is passed back through the self-cinching sleeve, forming a suture construct having a self-cinching section with four co-axially aligned segments of the suture strand radially housed together. By providing multiple passes of the suture strand material through the self-cinching section, mechanical constriction of the suture construct during tensioning is enhanced to prevent slippage under cyclic loading.

In further embodiments, a suture construct apparatus includes a suture strand including an adjustable loop at a first end and a fixed loop at a second end. A self-cinching section is disposed on the suture strand between the adjustable loop and the fixed loop, the self-cinching section includes first and second segments of the suture strand co-axially aligned. A first tag end of the suture strand extends axially inside both the first and second segments of the suture strand in the self-cinching section, and a second tag end of the suture strand is housed axially inside a portion of the first tag end.

In additional embodiments, a suture construct apparatus includes a suture strand including an adjustable loop at a first end and a fixed loop at a second end opposite the first end. A self-cinching section is disposed on the suture strand between the fixed loop and the adjustable loop, wherein the self-cinching section includes two or more co-axially aligned segments of the suture strand extending axially inside the self-cinching section.

In further embodiments, suture construct apparatus, includes a suture strand having a first tag end and a second tag end. An adjustable loop is formed by the first tag end. A fixed loop is formed by the second tag end. A self-cinching section is formed on the suture strand between the fixed loop and the adjustable loop, wherein a portion of the second tag end extends axially through the self-cinching section inside the suture strand toward the adjustable loop. The second tag end is housed in a portion of the first tag end passing through the self-cinching section toward the fixed loop, and at least two segments of the suture strand are co-axially aligned inside the self-cinching section of the suture strand.

Numerous other objects, advantages and features of the present disclosure will be readily apparent to those of skill in the art upon a review of the drawings and description as set forth below.

DETAILED DESCRIPTION

Figure 1:
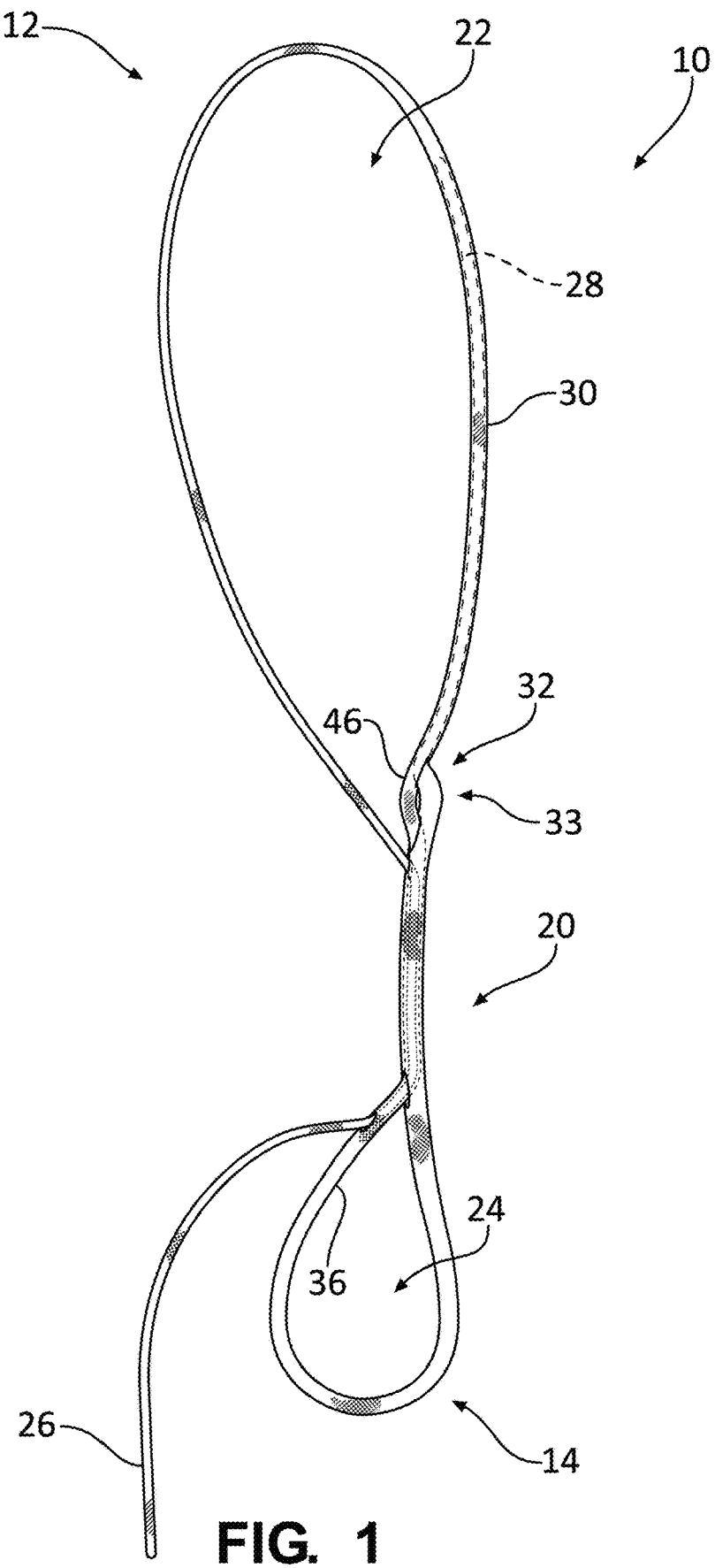
FIG. 1 illustrates an embodiment of a multiple pass self-cinching suture construct in accordance with the present disclosure.

The present disclosure provides various embodiments of improved self-cinching suture construct devices and methods for use in orthopedic surgery.

While the making and using of various embodiments of the present disclosure are discussed in detail herein, it should be appreciated that the present disclosure provides many applicable inventive concepts that are embodied in a wide variety of specific contexts. The specific embodiments discussed herein are merely illustrative of specific ways to make and use the disclosure and do not delimit the scope of the disclosure. Those of ordinary skill in the art will recognize numerous equivalents to the specific apparatuses, systems, and methods described herein. Such equivalents are considered to be within the scope of this disclosure and may be covered by the claims.

Furthermore, the described features, structures, or characteristics of the disclosure may be combined in any suitable manner in one or more embodiments. One skilled in the relevant art will recognize, however, that the disclosure may be practiced without one or more of the specific details, or with other methods, components, materials, apparatuses, devices, systems, and so forth. In other instances, well-known structures, materials, or operations may not be shown or described in detail to avoid obscuring aspects of the disclosure.

In the drawings, not all reference numbers are included in each drawing, for the sake of clarity. In addition, positional terms refer to the apparatus when in the orientation shown in the drawing. A person of skill in the art will recognize that the apparatus can assume different orientations when in use.

Referring to FIG. 1, an embodiment of a self-cinching adjustable loop suture construct 10 is illustrated. Suture construct 10 includes a first end 12 and a second end 14 opposite first end 12. An adjustable loop 22 is formed at first end 12, and a fixed loop 24 is formed at second end 14 opposite adjustable loop 22. A self-cinching section 20 is formed between adjustable loop 22 and fixed loop 24.

Suture construct 10 is formed from a single strand of suture material in some embodiments, such as but not limited to hollow core braided suture material of the type used in orthopedic surgery for procedures such as repair or reconstruction of ligaments. The single strand of suture material is mechanically arranged by passing the suture strand into and/or through itself to form a suture construct 10 for securing ligaments or tissue. By providing a suture construct 10 from a single strand of suture material in some embodiments, a complex adjustable loop suture construct with a robust self-cinching feature may be formed using only a single strand of material spliced and/or woven into or through itself. Such a configuration eliminates the need for multiple separate pieces of suture material. In other embodiments, suture construct 10 may be formed from multiple strands of suture material joined together to form the desired construction.

Referring further to FIG. 1, the suture strand includes a first tag end 26 and a second tag end 28. First tag end 26 is positioned extending from the suture construct 10 at a free position for tightening the suture construct, and specifically for tightening adjustable loop 22, by pulling on first tag end 26 when the suture construct is deployed at the surgical site or prior to installation. Second tag end 28 is housed inside the hollow interior of the suture strand in adjustable loop 22, forming a tag sleeve 30. Once housed axially inside tag sleeve 30, second tag end 28 is not removed from the tag sleeve 30, and second tag end 28 translates through self-cinching section 20 inside of first tag end 26 when the suture construct is tightened.

Figure 2:
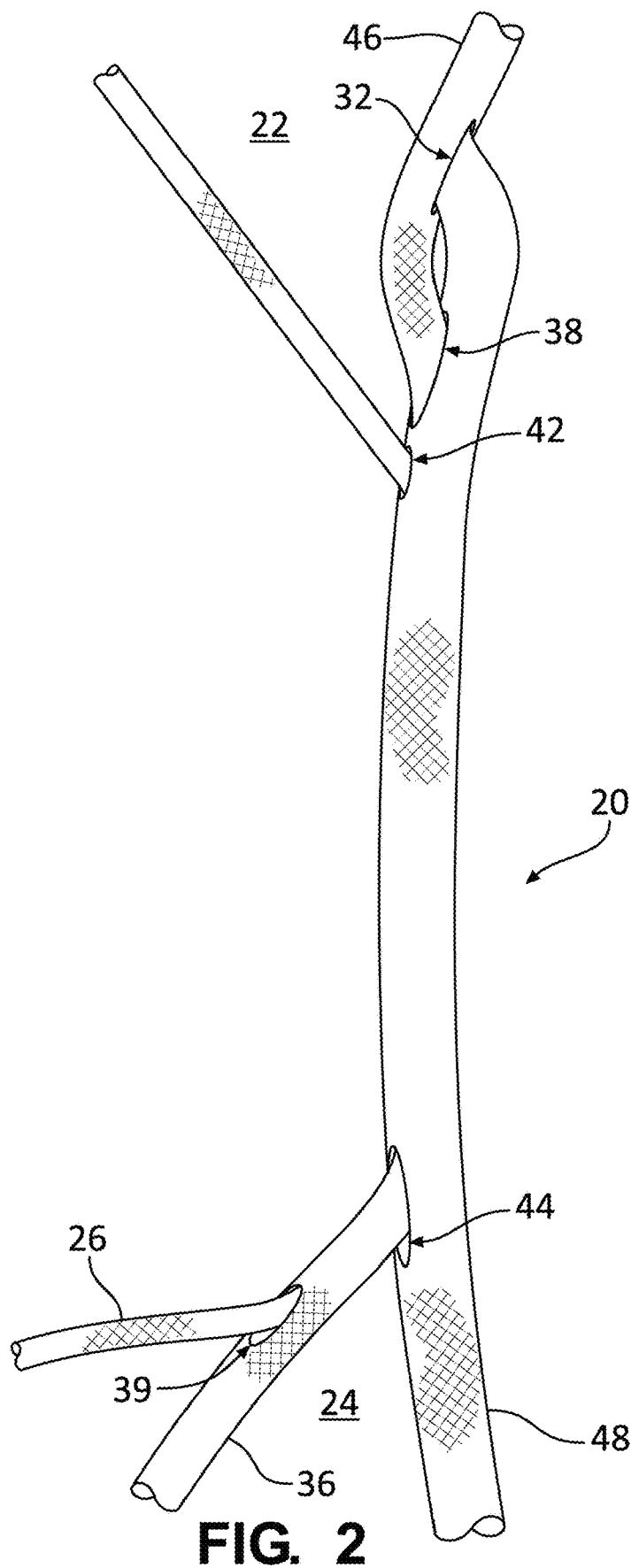
FIG. 2 illustrates a detail view of an embodiment of a self-cinching section of a multiple pass self-cinching suture construct in accordance with the present disclosure.
Figure 3:
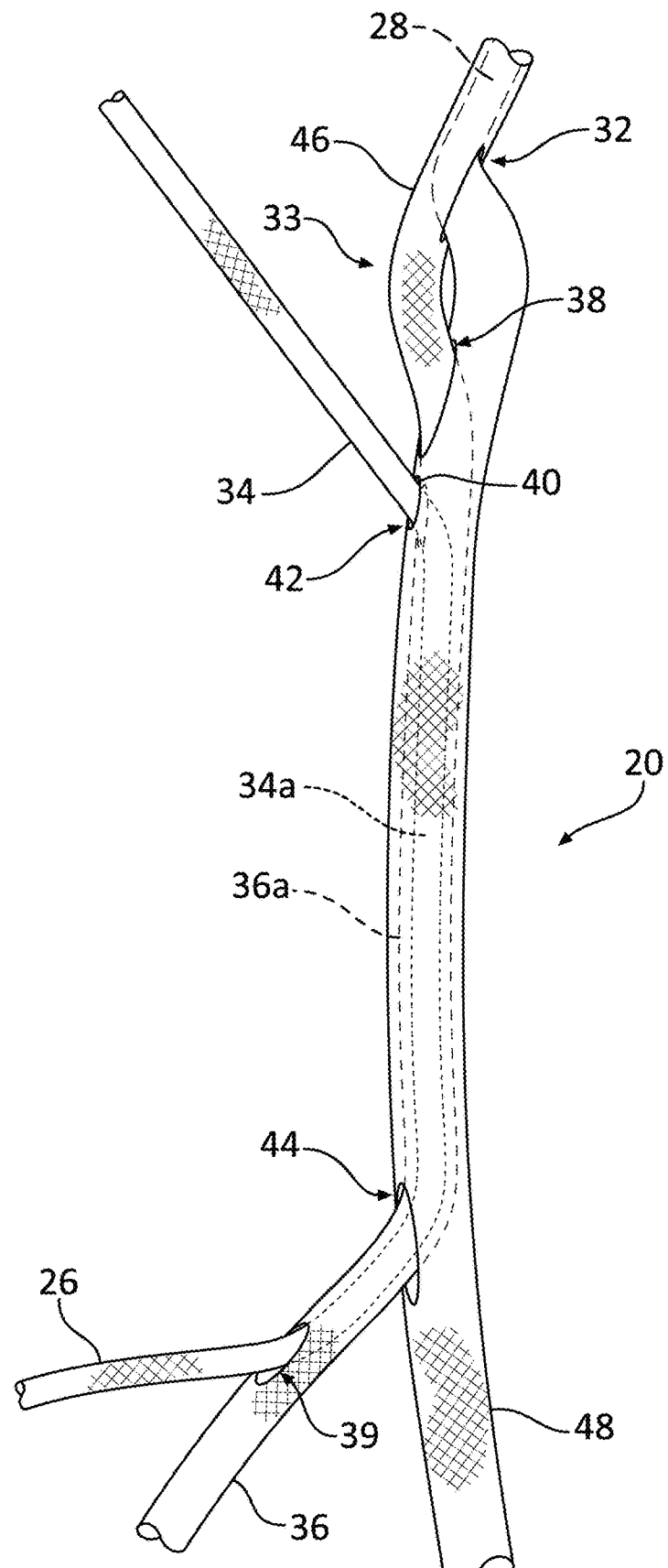
FIG. 3 illustrates a detail partial cross-sectional view of an embodiment a self-cinching section of a multiple pass self-cinching suture construct in accordance with the present disclosure.

Referring to FIGS. 1-3, a self-cinching section 20 is disposed in the suture strand between fixed loop 24 and adjustable loop 22. Self-cinching section 20 includes multiple axial passes of suture material through the hollow interior core of the suture strand along self-cinching section 20. A portion of the suture strand forming fixed loop 24 enters the self-cinching section 20 at first opening 44, and a section of suture material 36a travels axially through the self-cinching section 20 and exits the self-cinching section 20 at a second opening 38. The portion 46 exiting the self-cinching section 20 receives second tag end 28 at a third opening 32 defined in the portion 46 exiting the self-cinching section, thereby forming a locking joint 33 that establishes fixed loop 24 as a static loop that does not slip when tension is applied to the suture construct. The mechanical configuration of locking joint 33 causes second opening 38 and third opening 32 to collapse toward each other when tension is applied to the suture construct and prevents the suture strand from slipping, thereby providing a near one-hundred percent tensile strength at locking joint 33 to form fixed loop 24.

Figure 4:
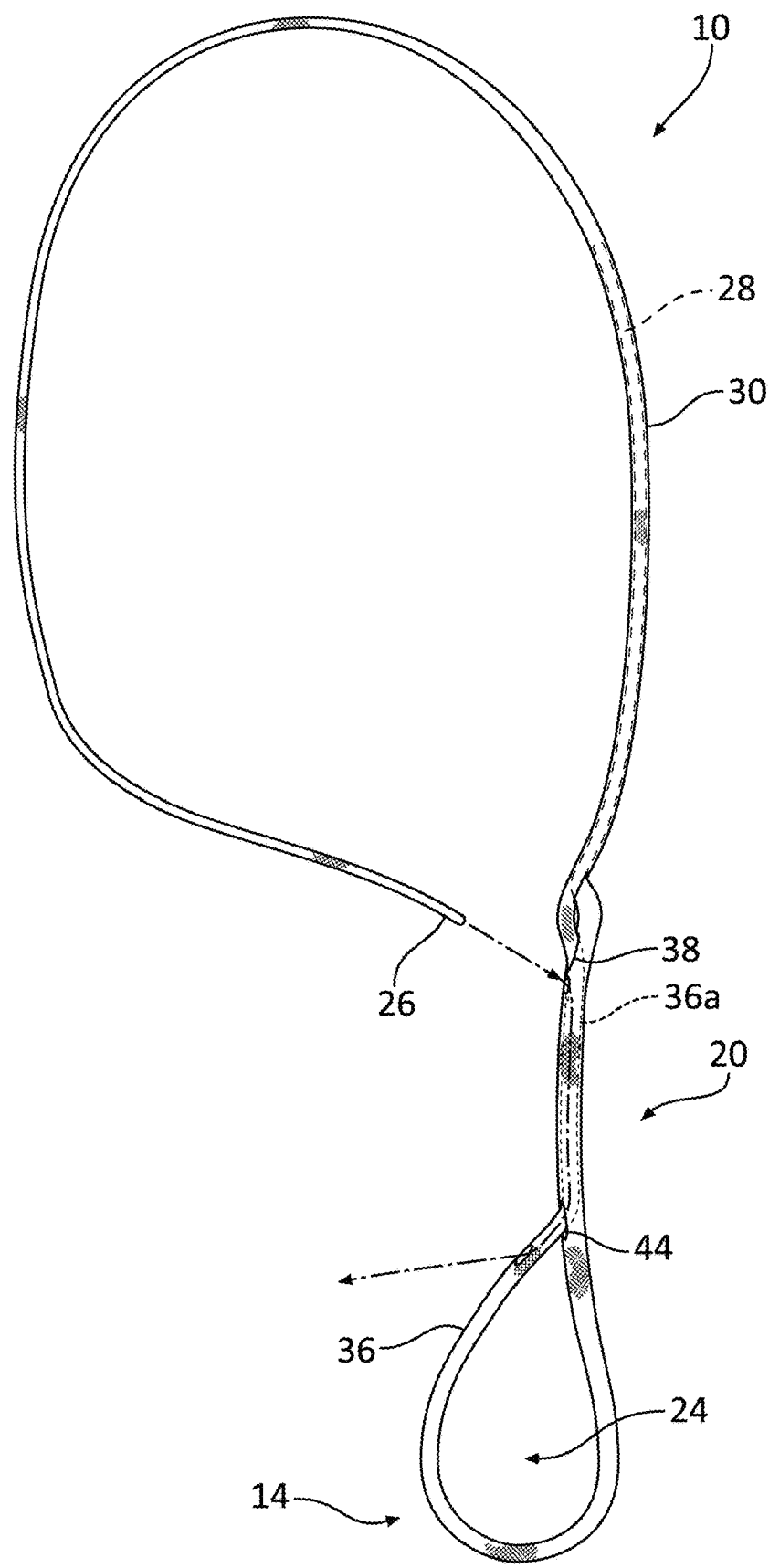
FIG. 4 illustrates an embodiment of a multiple pass self-cinching suture construct positioned for insertion of a first tag end back through the self-cinching section in accordance with the present disclosure.

Once second tag end 28 is housed inside tag sleeve 30, as shown in FIG. 4, first tag end 26 may be passed through self-cinching section 20, which already includes portion 36a extending axially through the interior of the self-cinching section 20. Specifically, first tag end 26 enters self-cinching section 20 at a fourth opening 42 (shown in FIG. 2 and FIG. 3) defined in the wall of the outermost suture material along self-cinching section 20 at an axial position between second opening 38 and first opening 44.

First tag end 26 is passed through both the outer suture wall via fourth opening 42 and also through the interior wall of portion 36a into the innermost hollow bore on the interior of portion 36a via a fifth opening 40 which is defined in portion 36a housed inside the self-cinching section 20. From this position, first tag end 26 is advanced axially through the innermost hollow bore of portion 36a toward second end 14. In some embodiments, first tag end 26 extends along the interior of portion 36a and exits first opening 44 while still remaining inside the interior hollow bore of fixed loop portion 36 along the fixed loop 24 adjacent first opening 44. First tag end 26 then exits through a sixth opening 39 and extends freely at a position exterior of first opening 44 and sixth opening 39 along the length of fixed loop portion 36 on the fixed loop 24. From this position, first tag end 26 may be pulled to tension the adjustable loop 22 on the suture construct 10.

Figure 5:
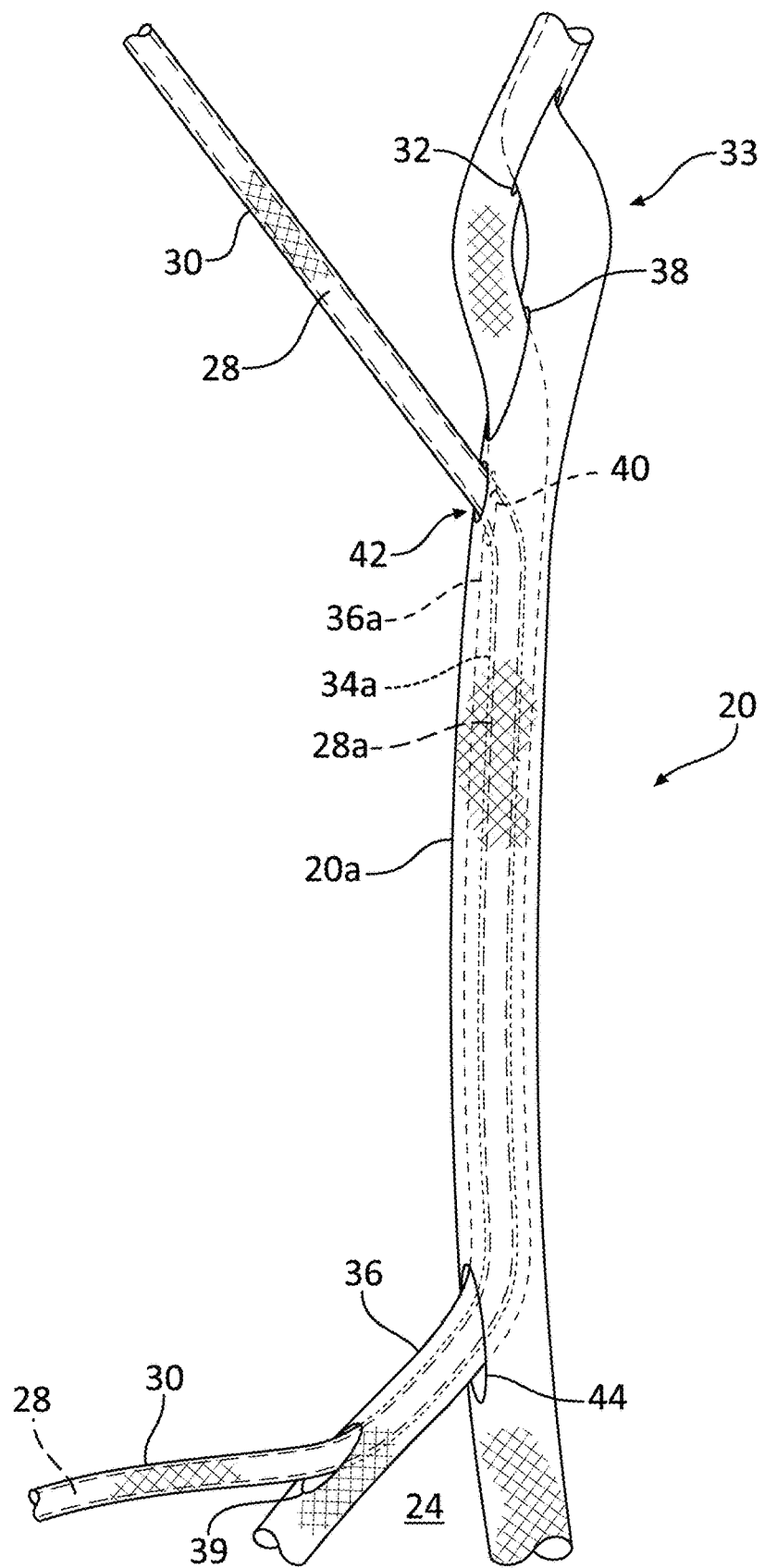
FIG. 5 illustrates a detail partial cross-sectional view of an embodiment of a self-cinching section of a multiple pass self-cinching suture construct including a first tag end (with a second tag end housed therein) passing through the self-cinching section and exiting along the fixed loop in accordance with the present disclosure.

Referring to FIG. 4 and FIG. 5, from the position shown in FIG. 1, the first tag end 26 may be pulled such that the portion of adjustable loop 22 including second tag end 28 housed inside tag sleeve 30 approaches and enters fourth opening 42, extends into fifth opening 40, passes through the axial length of self-cinching section 20 toward second end 14, exits through first opening 44 (while still inside the fixed loop portion 36), and exits the fixed loop 24 through sixth opening 39. In this configuration, self-cinching section 20 is defined between first opening 44 and fourth opening 42. Self-cinching section 20 includes four portions of suture strand co-axially aligned inside each other. From the radial center in an outer direction, the innermost segment includes a portion 28a of second tag end 28. The next segment includes a portion 34a of tag sleeve 30 in which second tag end 28 is housed. The next segment includes a section of suture material 36a formed by the first splicing pass of the suture strand through the self-cinching section 20 to form fixed loop 24. The outermost segment includes a portion 20a of the main body of the self-cinching section 20. As such, self-cinching section includes four segments of the suture strand extending co-axially aligned inside each other.

The configuration of self-cinching section 20 may be referred to as a double pass configuration, or a multiple pass configuration, because the first tag end 26 is inserted into the internal bore of not just one, but two co-axially aligned suture segments via fourth and fifth openings 42, 40. Additionally, the suture construct may be referred to as a double pass configuration, or a multiple pass configuration, because when first tag end 26 is passed through the self-cinching section 20, it is carrying inside it the second tag end 28 housed in tag sleeve 30. Thus, by pulling first tag end 26 through the self-cinching section 20, two co-axial sections of suture material are actually being pulled through self-cinching section simultaneously. Such a double pass, or multiple pass, configuration provides enhanced constriction when tightening the suture construct 10. The configuration also accommodates a greater tensile strength for maintaining tension to ligaments or tissue once tightened. The configuration provides a mechanical "finger-trap" mechanism whereby the self-cinching section 20 constricts against the first tag end 26 passing through the self-cinching section 20 when tension is applied to the suture construct 10. Additionally, the presence of the second tag end 28 housed inside tag sleeve 30 passing through self-cinching section 20, as shown in FIG. 5, provides additional enhancement of the tightening of self-cinching section 20 and further prevents slippage of the suture construct during use.

Figure 6:
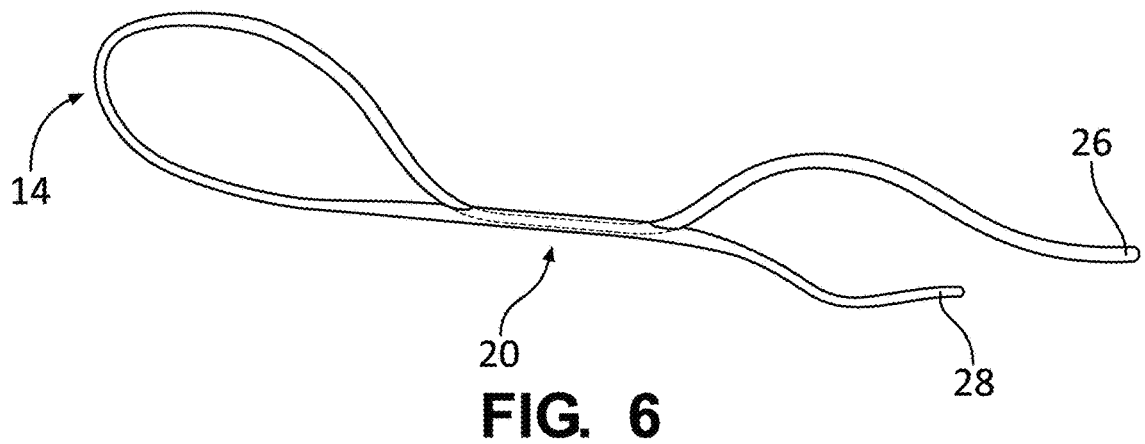
FIG. 6. illustrates a first step in constructing an embodiment of a multiple pass self-cinching suture construct and forming a fixed loop in accordance with the present disclosure.
Figure 7:
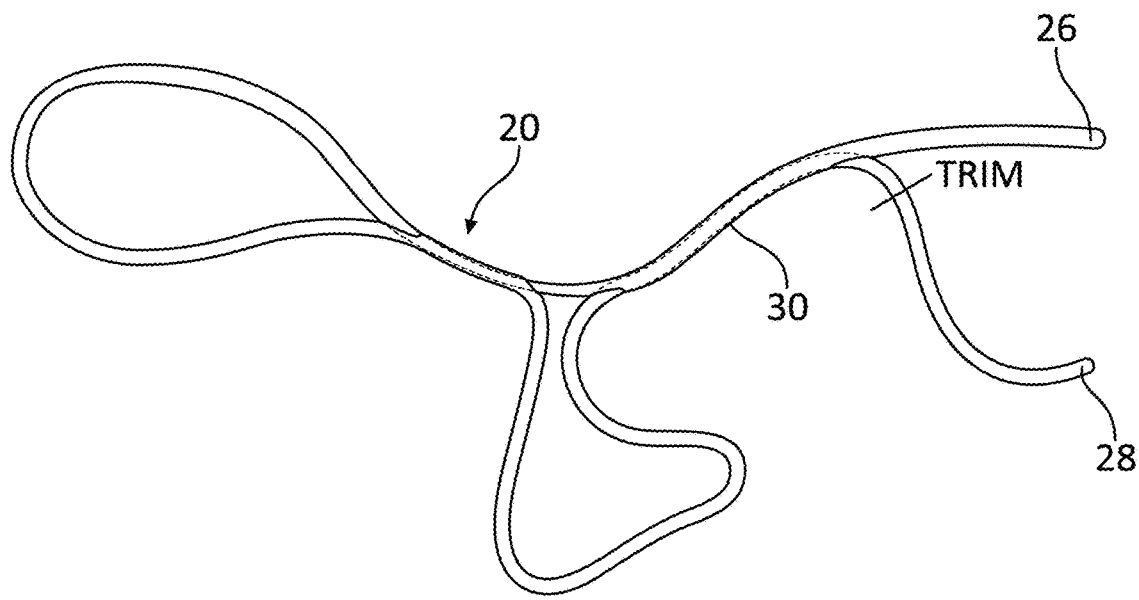
FIG. 7 illustrates a second step in constructing an embodiment of a multiple pass self-cinching suture construct and forming a fixed loop in accordance with the present disclosure.
Figure 8:
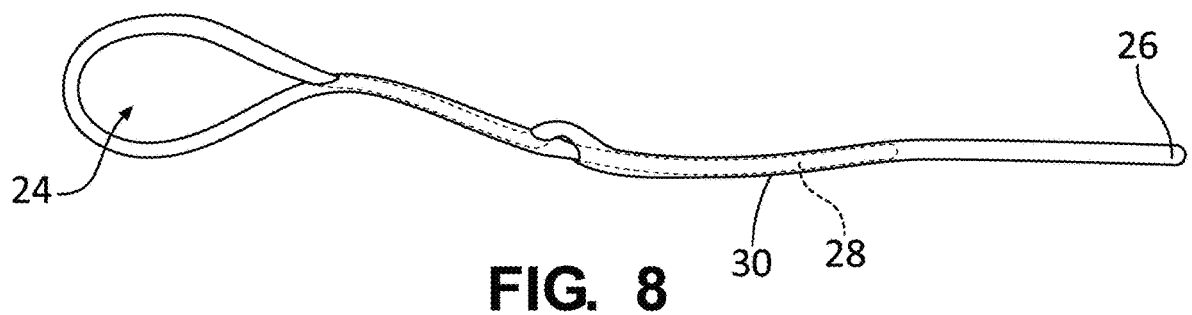
FIG. 8 illustrates a third step in constructing an embodiment of a multiple pass self-cinching suture construct and forming a fixed loop in accordance with the present disclosure.

Referring to FIGS. 6-8, an embodiment of the suture construct 10 during a first step of formation of fixed loop 24 is illustrated. The single strand of suture material is folded in a 180-degree turn such that first tag end 26 and second tag end 28 are oriented in the same direction, forming a bend in the second end 14. First tag end 26 is spliced axially through a section of the internal hollow bore of the suture strand, thereby forming a region that will define self-cinching section 20. From this position, second tag end 28 is inserted into the internal hollow bore of first tag end 26, thereby forming tag sleeve 30, as shown in FIG. 7. From this position, second tag end 28 may be pulled in a direction away from second end 14 and trimmed at an appropriate length, thereby seating second tag end 28 entirely inside tag sleeve 30 on the suture construct, and forming fixed loop 24, as shown in FIG. 8. From this position, shown in FIG. 8, the suture construct is prepared for the next step of passing first tag end 26 (with second tag end 28 housed inside tag sleeve 30) back through self-cinching section 20 toward second end 14 to form the adjustable loop.

Figure 9:
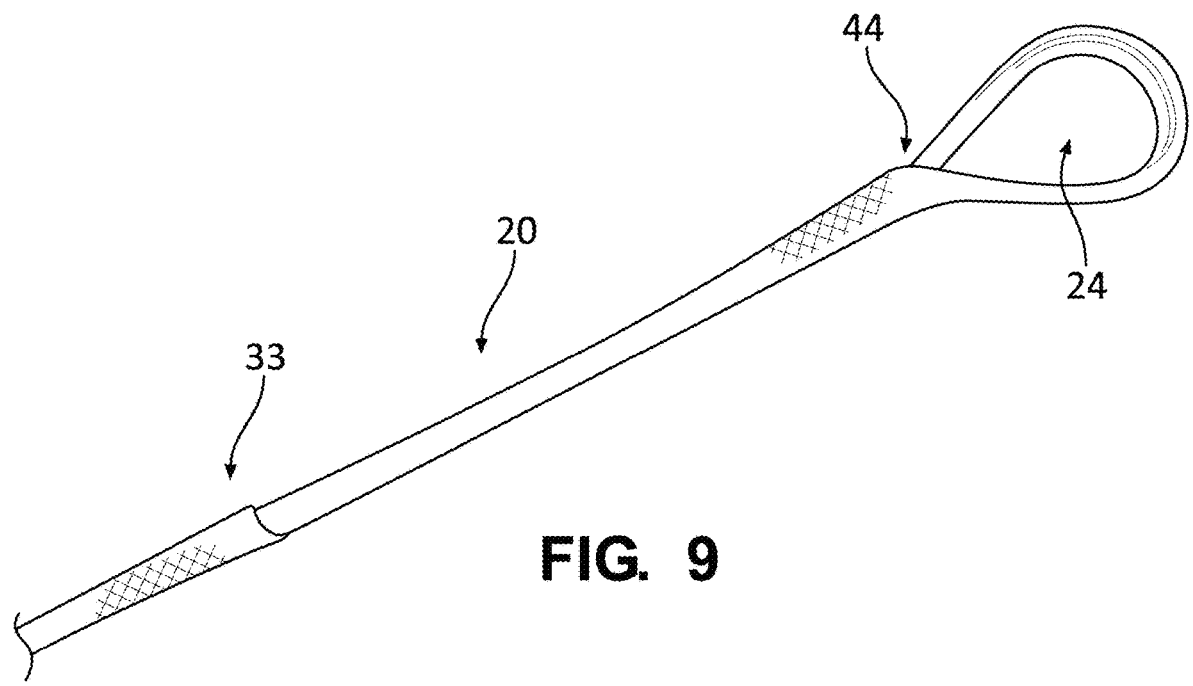
FIG. 9 illustrates an embodiment of a fixed loop of a multiple pass self-cinching suture construct in accordance with the present disclosure.

Referring to FIG. 9, an embodiment of a portion of the suture strand including fixed loop 24 is shown, including a portion of the suture strand entering first opening 44, passing through self-cinching section 20, and forming locking joint 33.

Figure 10:
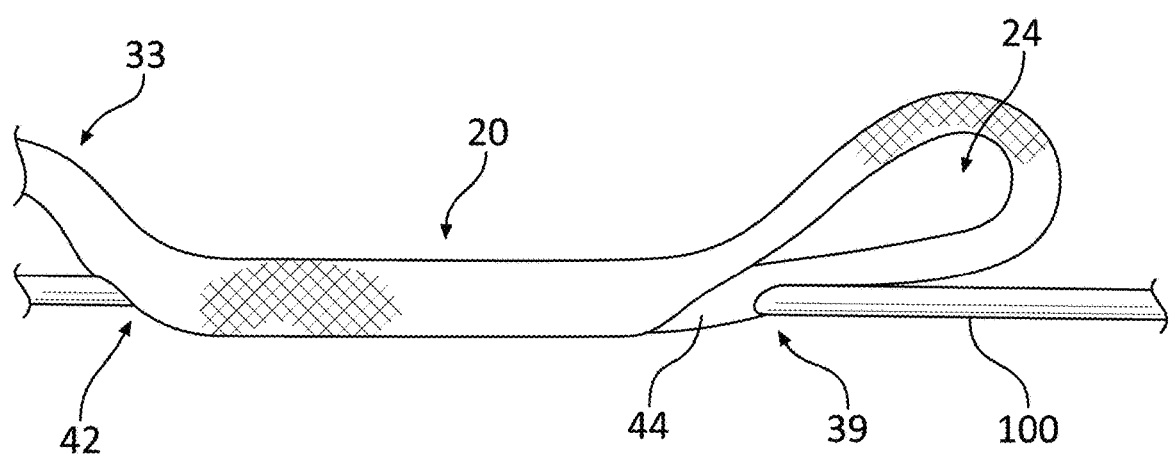
FIG. 10 illustrates a step of advancing a passing needle through an embodiment of a self-cinching section of a multiple pass self-cinching suture construct in accordance with the present disclosure.

Referring to FIG. 10, a next step in forming the suture construct is shown to prepare for passage of the first tag end 26 through self-cinching section 20. A passing, or splicing, needle 100 is inserted into a portion of the fixed loop 24 near first opening 44 in some embodiments, thereby forming sixth opening 39. The passing needle 100 is inserted axially through the interior of the innermost segment passing axially through self-cinching section 20, and the passing needle 100 exits self-cinching section at a location between locking joint 33 and first opening 44 near locking joint 33, thereby forming fourth opening 42.

Figure 11:
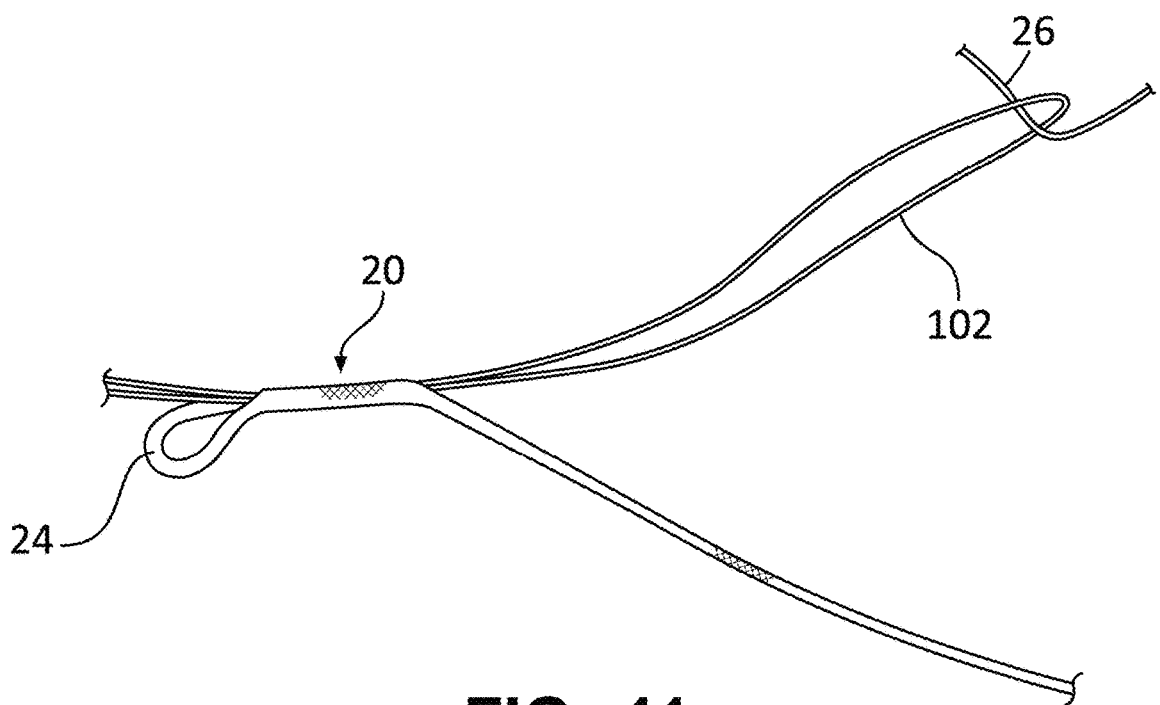
FIG. 11 illustrates a step of engaging a first tag end with a passing suture to advance the first tag end through an embodiment of a self-cinching section of a multiple pass self-cinching suture construct in accordance with the present disclosure.
Figure 12:
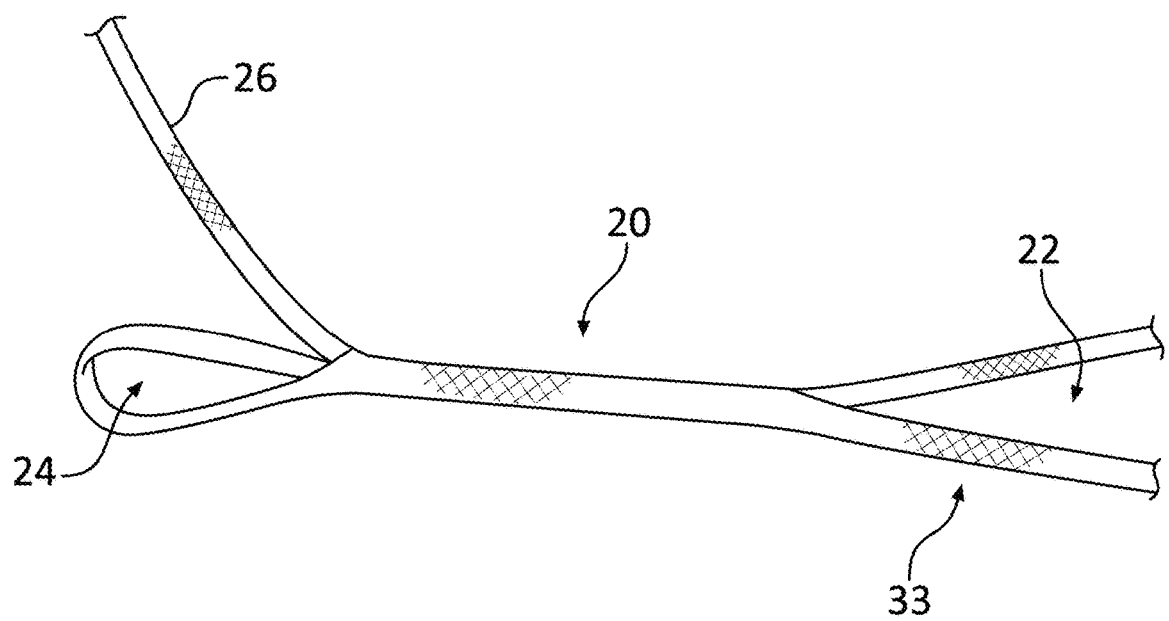
FIG. 12 illustrates an embodiment of a multiple pass self-cinching suture construct in accordance with the present disclosure.

Referring to FIG. 11, a passing suture 102 is introduced, via passing needle 100, through the same internal path taken by passing needle 100. Passing suture 102 is looped at one end, and tag end 26 is placed in the loop formed by passing suture 102. From this position, the passing suture 102 can be pulled back through the self-cinching section 20 toward fixed loop 24 to advance tag end 26 axially through self-cinching section 20, resulting in the multiple pass self-cinching suture construct configuration shown in FIG. 12.

Figure 13:
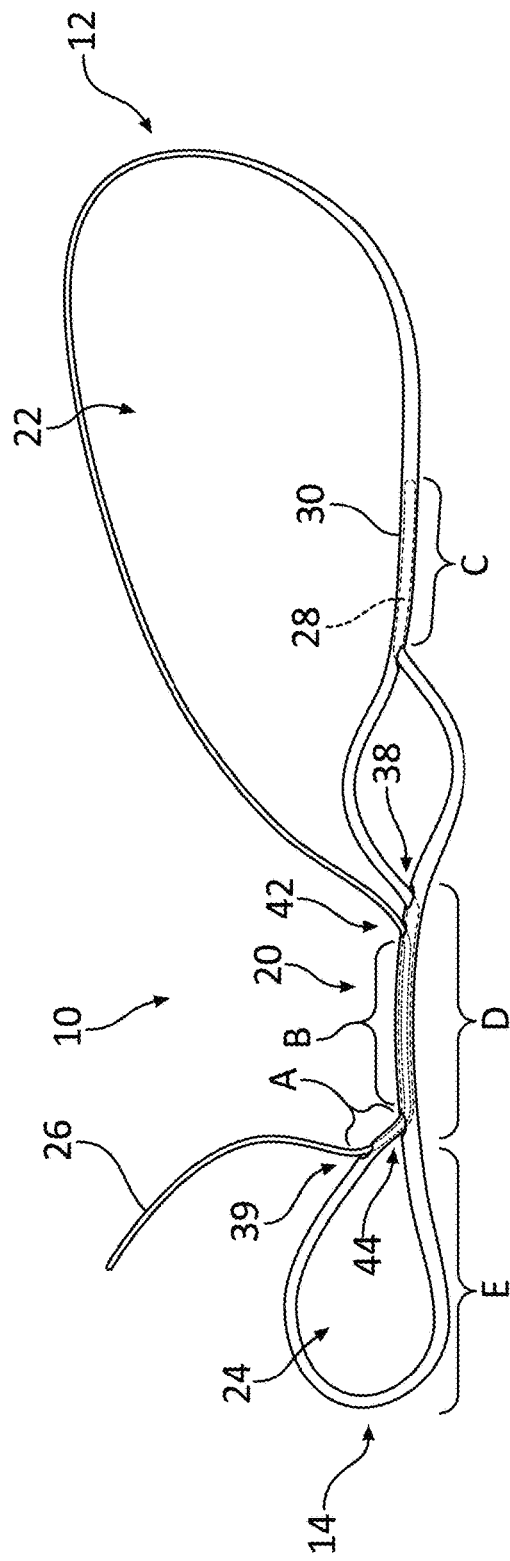
FIG. 13 illustrates an embodiment of a multiple pass self-cinching suture construct including dimensional features in accordance with the present disclosure.

Referring to FIG. 13, an embodiment of a suture construct 10 is illustrated with exemplary dimensions identified by letters A, B, C, D and E. The following dimensions are provided as possible embodiments, and in practice, the suture construct 10 may include variations to the dimensions described herein, as would be appreciated by those of skill in the art, for specific types of orthopedic procedures or different anatomy. In some embodiments, the distance A between first opening 44 and sixth opening 39 is about one millimeter, the axial length B of self-cinching section 20 between first opening 44 and fourth opening 42 is about nine millimeters, the axial length C of the second tag end 28 housed inside tag sleeve 30 between second opening 38 and the distal end of second tag end 28 is about one-hundred millimeters (not shown to scale). Additionally, the axial length D of the initial splice between first opening 44 and second opening 38 is about twenty millimeters, and the length of the fixed loop E from second end 14 to first opening 44 is about seven millimeters. The length of adjustable loop 22 may vary, and in some embodiments, the length of adjustable loop 22 between fourth opening 42 and first end 12 (prior to tensioning) is about one-hundred twenty millimeters.

Figure 14:
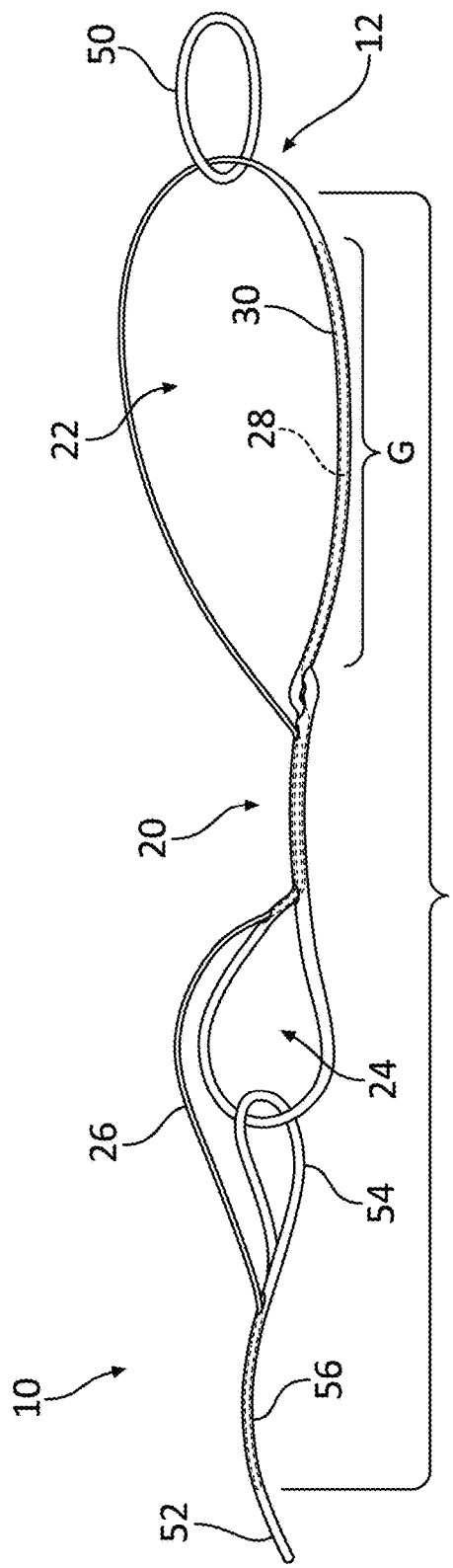
FIG. 14 illustrates an embodiment of a multiple pass self-cinching suture construct including tapered features in accordance with the present disclosure.

Referring to FIG. 14, in some embodiments, a continuous loop 50 is disposed on adjustable loop 22. Continuous loop 50 may be secured directly to a ligament or to an anchor such as a suture anchor or suture button. Continuous loop 50 includes a ring-shaped suture construct freely disposed on the adjustable loop 22 such that the suture construct may slide freely through continuous loop 50. Additionally, a shuttling suture 52 is disposed on fixed loop 24 in some embodiments. Shuttling suture 52 includes a shuttling suture loop 54 extending through fixed loop 24. The distal end of first tag end 26 may be inserted into the hollow interior core of shuttling suture 52, forming a shuttling suture sleeve 56 which houses and protects first tag end 26 as the suture construct is passed through tissue or through an anchoring device.

Referring further to FIG. 14, in some embodiments, the suture strand forming the suture construct 10 may include tapering to provide enhanced operation and deployment. In some embodiments, second tag end 28 includes a progressive narrowing taper G inside tag sleeve 30. Additionally, the first tag end 26 extending from first end 12 to the distal end of first tag end 26 includes a progressive narrowing taper.

Figure 15:
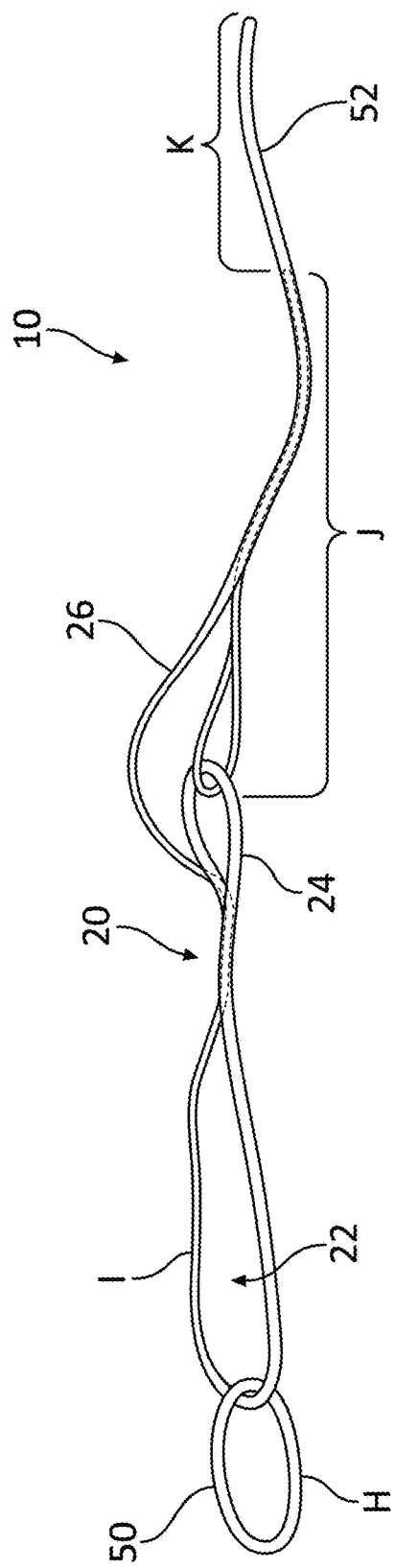
FIG. 15 illustrates an embodiment of a multiple pass self-cinching suture construct including color-coded features in accordance with the present disclosure.

Referring to FIG. 15, in some embodiments, suture construct 10 includes color coding at different locations along the strand of suture material. In some embodiments, continuous loop, or free loop 50 includes a first color or pattern H, and adjustable loop 22 includes a second color or pattern I different from the first color or pattern. Shuttling suture 52 includes a third color or pattern J different from the first and second colors or patterns, extending from fixed loop 24 to an intermediate position along the length of shuttling suture 52 where the first tag end 26 terminates inside the interior hollow core of the shuttling suture 52. The remaining portion of shuttling suture 52 includes a fourth color or pattern K different from the first, second and third colors or patterns. The two different colors or patterns, J and K, on shuttling suture 52 designate a location where a user may load the suture in a passing device. In some embodiments, color H is black with white check pattern, color I is black with a blue check pattern, color J is white with black check pattern, and color K is all white. Other suitable colors and/or patterns may be used to distinguish between colors H, I, J and K.

Figure 16:
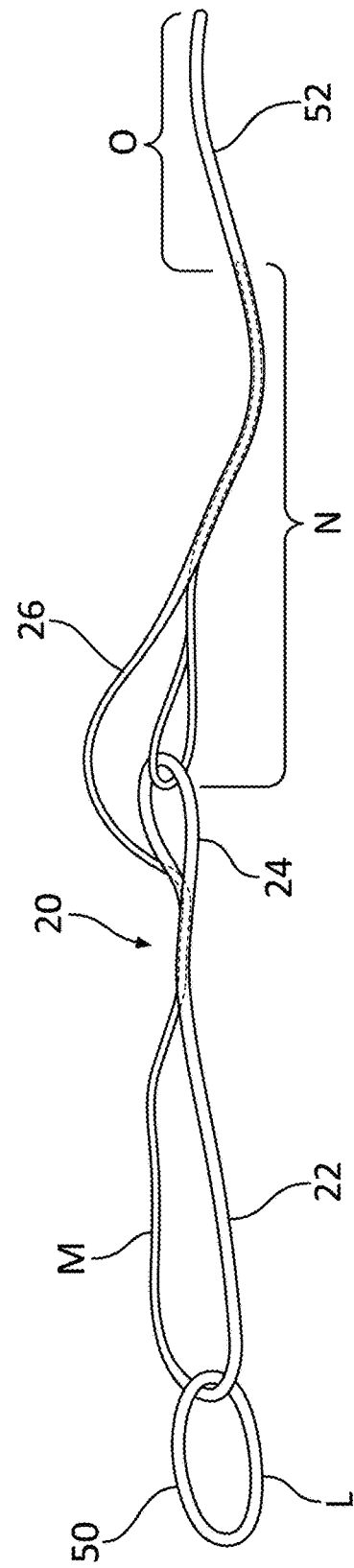
FIG. 16 illustrates an embodiment of a multiple pass self-cinching suture construct including color-coded features in accordance with the present disclosure.

Referring to FIG. 16, in some embodiments, an alternative color scheme may be used, including color L being black with a white check pattern on continuous loop 50, color M being black with a blue check pattern on adjustable loop 22, color N being white with a black check pattern on a first portion of shuttling suture 52, and color O being all white on a second portion of shuttling suture 52.

Figure 17:
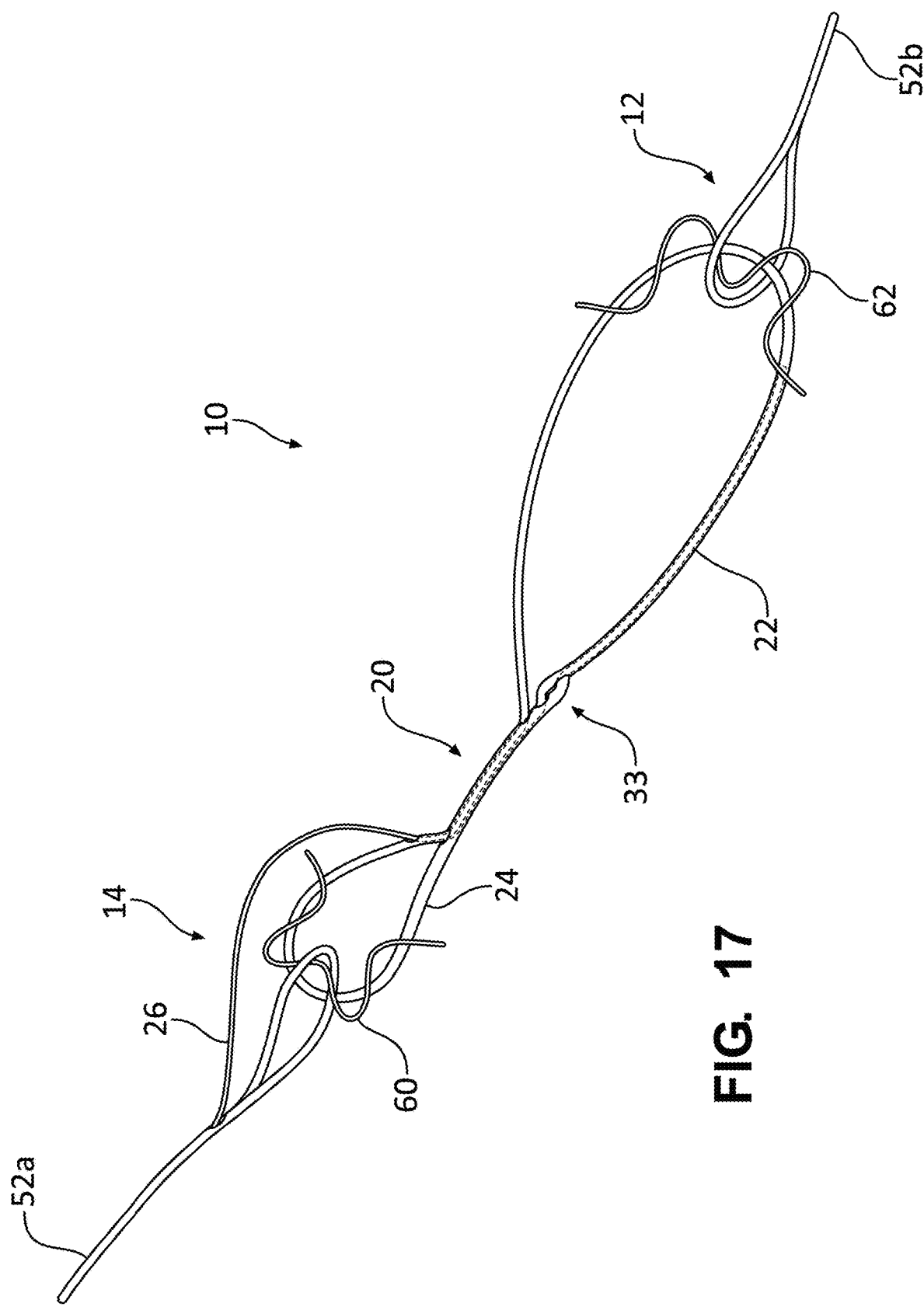
FIG. 17 illustrates an embodiment of a multiple pass self-cinching suture construct configured for fracture reduction in accordance with the present disclosure.

In some applications, a multiple pass self-cinching suture construct in accordance with the present disclosure is combined with one or more anchors for performing a surgical procedure. Referring to FIG. 17, an embodiment of a multiple pass self-cinching suture construct 10 includes the main suture construct as described herein with respect to FIGS. 1-5, and also including a first shuttling suture 52a disposed on fixed loop 24 at second end 14, a second shuttling suture 52b disposed on adjustable loop 22 at first end 12, a first anchor 60 disposed on fixed loop 24, and a second anchor 62 disposed on adjustable loop 22. First and second anchors 60, 62 may include any suitable fixation anchor known in the art, such as but not limited to a rigid anchor, suture button or a soft anchor. In some embodiments, each anchor may include suture tape, suture material, metal, metal button, metal alloy, plastic, polymer, polyether-ether-ketone (PEEK), bioresorbable material, a button, screw, implant, late, graft, tissue graft, orthopedic device, needle, suture loop, shuttling suture, hollow suture or a suture anchor. As shown in FIG. 17, in some embodiments, first and second anchors 60, 62 include a soft anchor comprising a piece of flat suture tape or suture material threaded onto the suture forming suture construct 10 in multiple transverse passes of the suture material. Additionally, first shuttling suture 52a includes an end loop extending around first anchor 60 through fixed loop 24, and second shuttling suture 52b includes an end loop extending around second anchor 62 through adjustable loop 22. Such a configuration may be used for fracture reduction.

Figure 18:
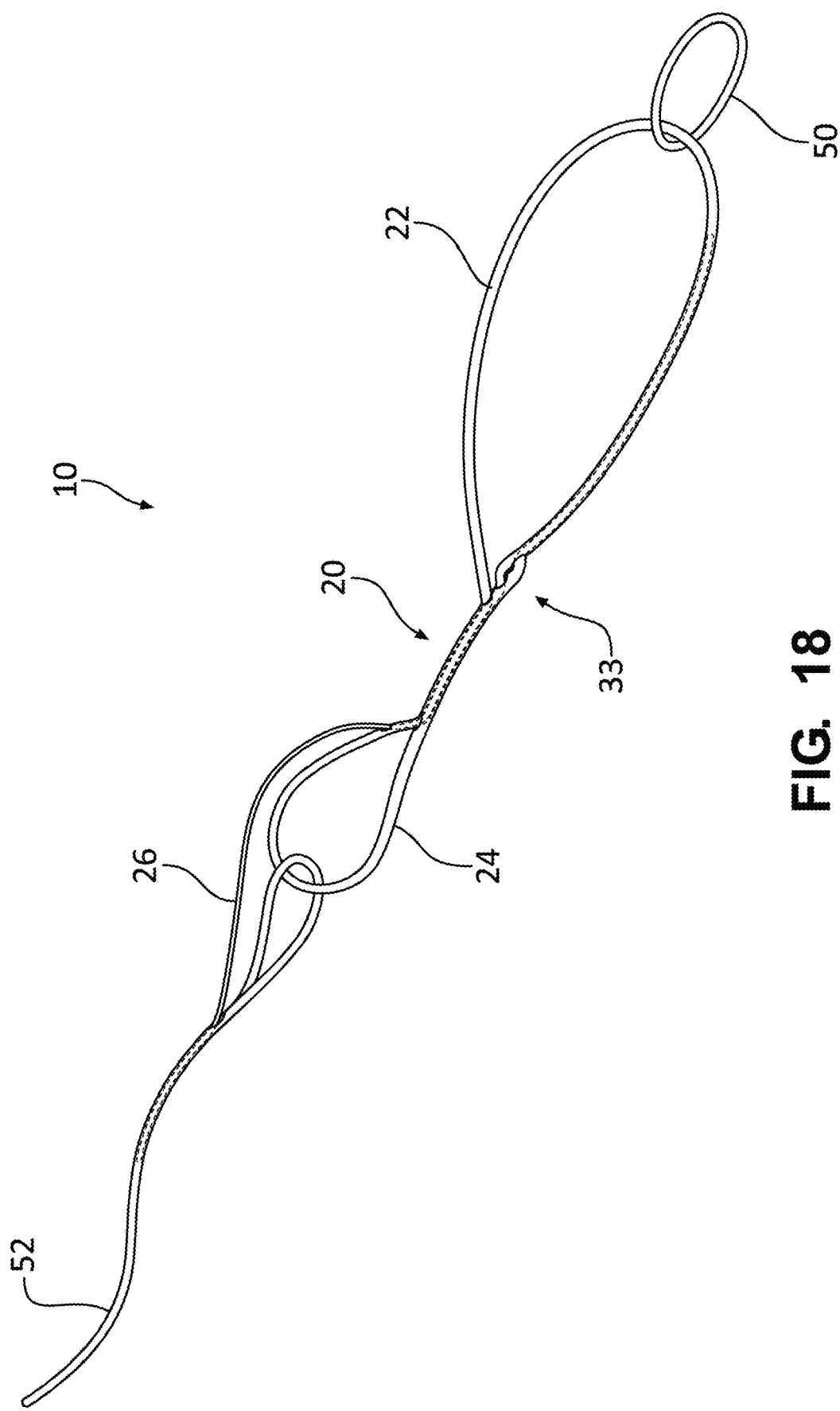
FIG. 18 illustrates an embodiment of a multiple pass self-cinching suture construct configured for meniscal root or anterior cruciate ligament (ACL) repair or reconstruction in accordance with the present disclosure.

Referring to FIG. 18, in some alternative embodiments, a multiple pass self-cinching suture construct 10 includes a shuttling suture 52 disposed on fixed loop 24, and a continuous loop 50 is disposed on adjustable loop 22. Such configurations may be used for meniscal root repair or repair or reconstruction of the anterior cruciate ligament (ACL).

Figure 19:
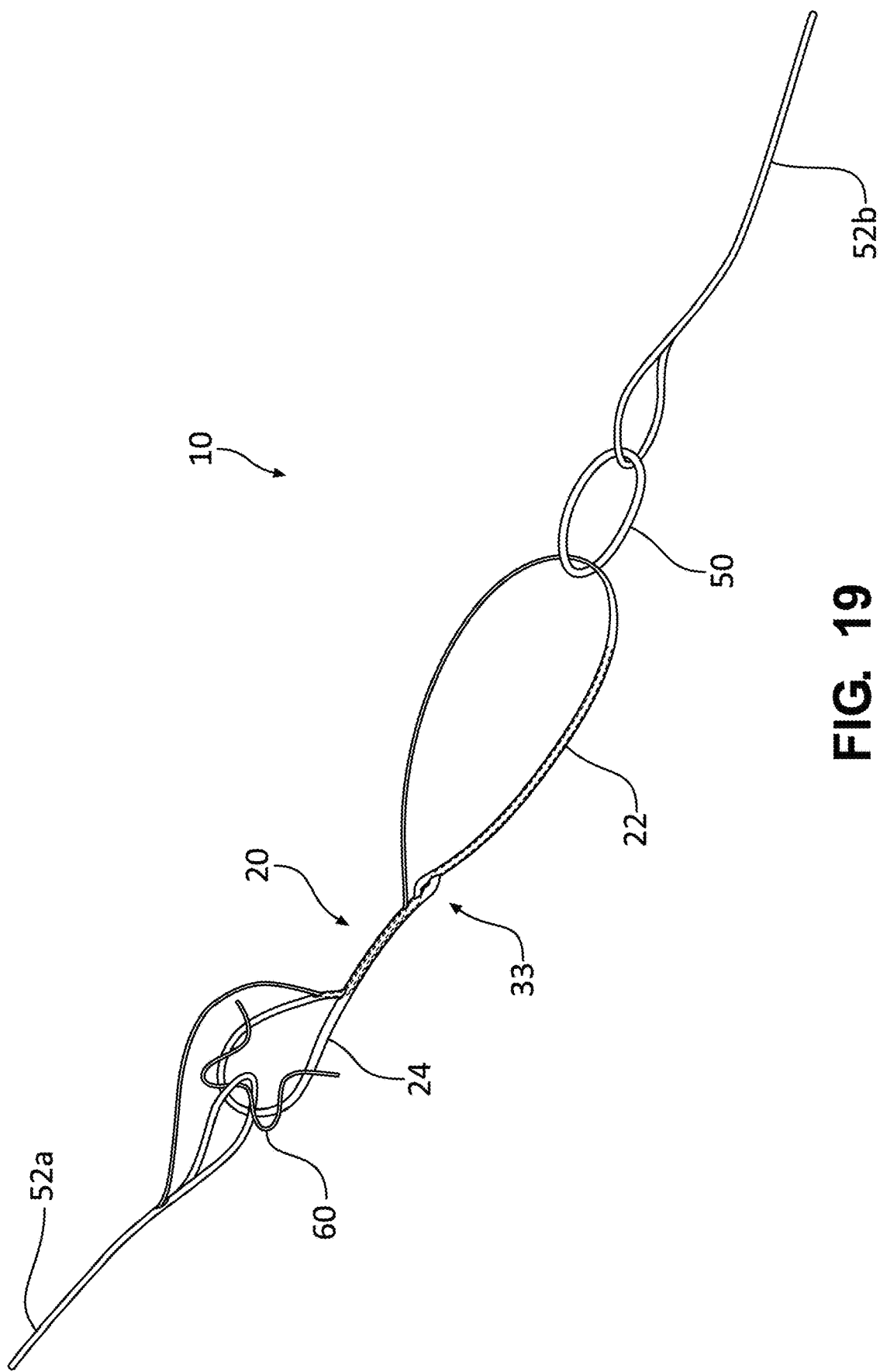
FIG. 19 illustrates an embodiment of a multiple pass self-cinching suture construct including a soft anchor in accordance with the present disclosure.

Referring to FIG. 19, in some alternative embodiments, a multiple pass self-cinching suture construct 10 includes a first shuttling suture 52a disposed on fixed loop 24, including an anchor 60 also disposed on fixed loop 24 such that an end loop of first shuttling suture 52a extends around anchor 60 and through fixed loop 24. A continuous loop 50 is disposed on adjustable loop 22, and a second shuttling suture 52b is disposed on continuous loop 50. In some embodiments, anchor 60 includes a soft anchor such as a section of flat suture tape or suture material including multiple transverse passes of the suture material forming fixed loop 24 extending through the suture tape.

In some applications, the fixed loop 24 may be secured to any suitable anchor for various types of orthopedic procedures. For example, in some embodiments, an anchor such as a surgical button is secured to fixed loop 24 to maintain tension on the suture construct when tightened. However, in other embodiments, fixed loop 24 may be secured to a bone anchor to facilitate sub-cortical fixation. Additionally, due to the multiple pass configuration and enhanced mechanical constriction of self-cinching section 20, the axial length of self-cinching section 20 may be shortened while still retaining adequate tightening, thereby allowing the suture construct 10 to be used for a variety of orthopedic procedures.

Figure 20:
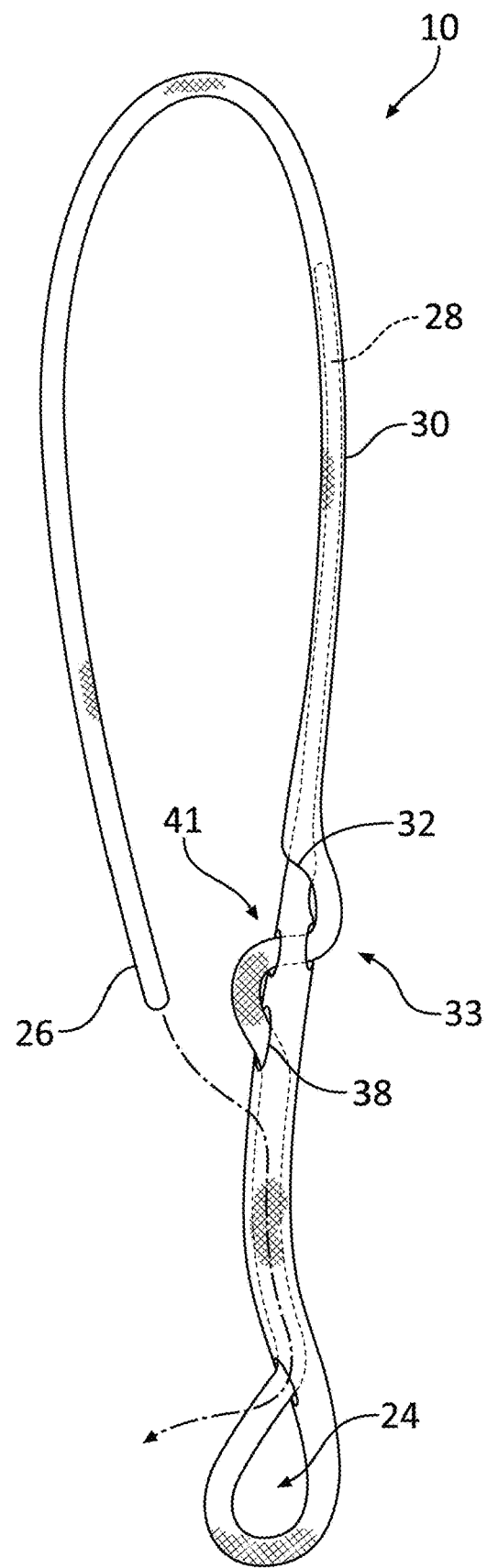
FIG. 20 illustrates an embodiment of a multiple pass self-cinching suture construct positioned for insertion of a first tag end back through the self-cinching section, including an alternative configuration for a locking joint, in accordance with the present disclosure.

Referring to FIG. 20, in some embodiments, suture construct 10 includes an alternative version of locking joint 33, wherein the second tag end 28 exiting second opening 38 makes a transverse pass 41 through the body of the adjacent suture portion before entering third opening 32 and extending into tag sleeve 30. The additional transverse pass 41 between third opening 32 and second opening 38 provides enhanced engagement between the overlapping suture strand portions at locking joint 33, thereby further tightening the locking joint 33 when the locking joint 33 is collapsed under tension.

Figure 21:
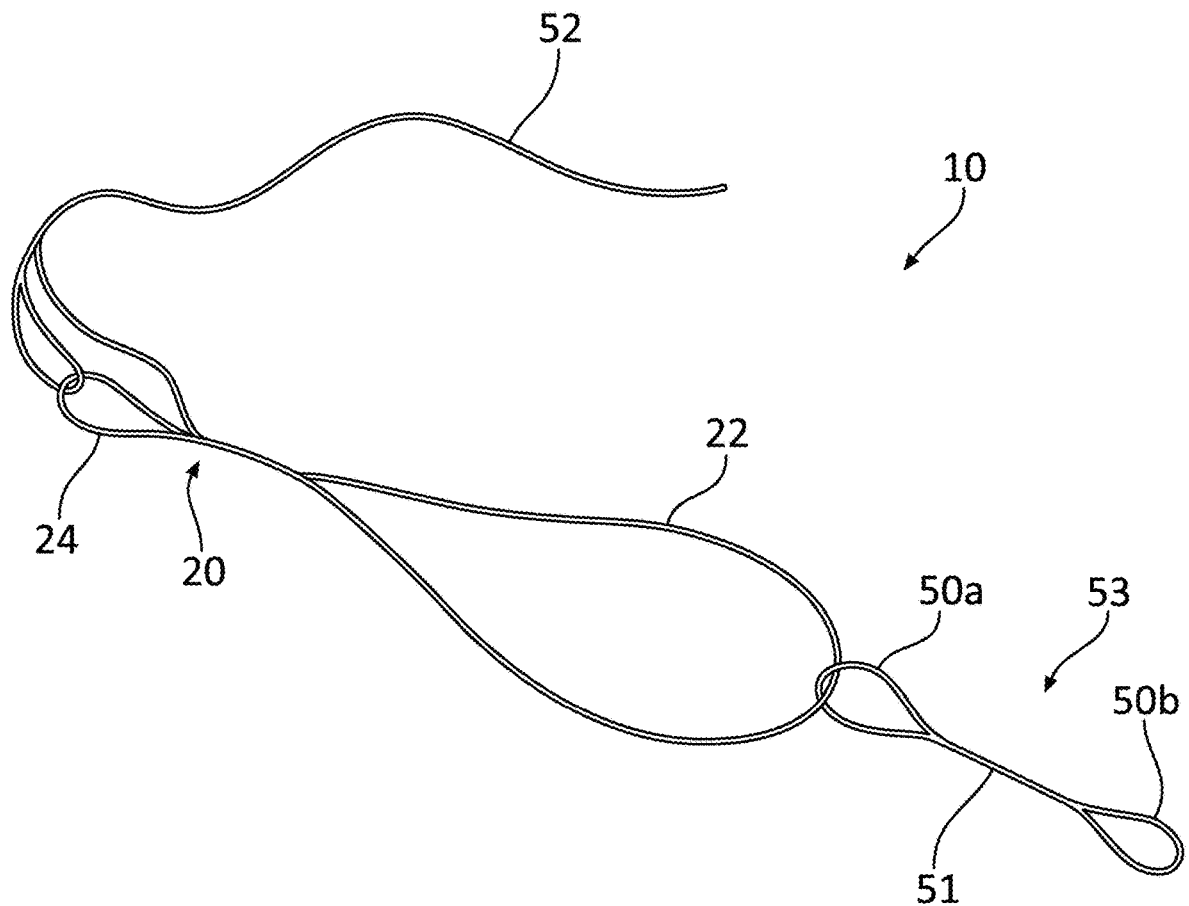
FIG. 21 illustrates an embodiment of a multiple pass self-cinching suture construct with an alternative embodiment of double free loop disposed on the adjustable loop in accordance with the present disclosure.
Figure 22:
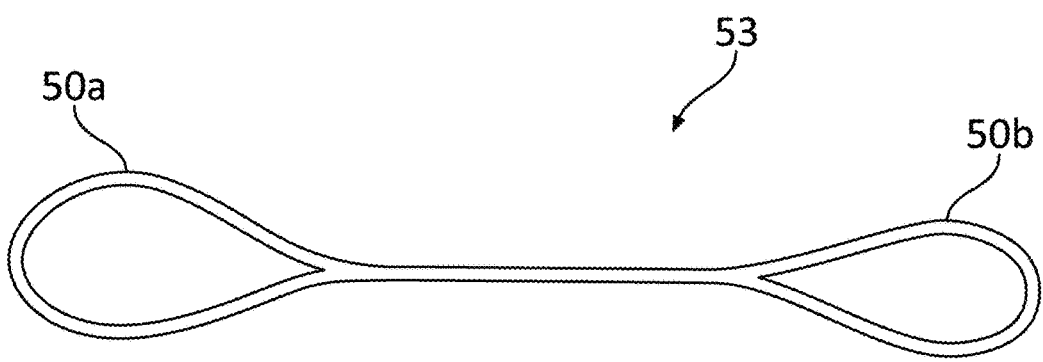
FIG. 22 illustrates an embodiment of a double free loop for use on a self-cinching suture construct in accordance with the present disclosure.

Referring to FIG. 21 and FIG. 22, in some embodiments, a multiple pass self-cinching suture construct 10 includes a single strand of suture material forming a fixed loop 24 and an adjustable loop 22, with a multiple pass self-cinching section 20 between the fixed loop 24 and the adjustable loop 22. A shuttling suture 52 is disposed on the fixed loop 24. Instead of a single ring-shaped continuous loop disposed on the adjustable loop, a double free loop 53 is disposed on adjustable loop 22. The double free loop 52 includes a first fixed loop 50a disposed on adjustable loop 22, and a second fixed loop 50b is positioned opposite first fixed loop 50a. First and second fixed loops 50a, 50b are separated by a connecting segment 51. In some embodiments, double free loop 53 includes hollow core braided suture material, and first and second fixed loops 50a, 50b are formed by splicing tag ends of the suture material back into the connecting segment 51 in one or more axial or transverse passes to form first and second fixed loops 50a, 50b. In some embodiments, double free loop 53 may be sewn into tissue or secured to an anchor at first or second fixed loop 50a, 50b.

Figure 23:
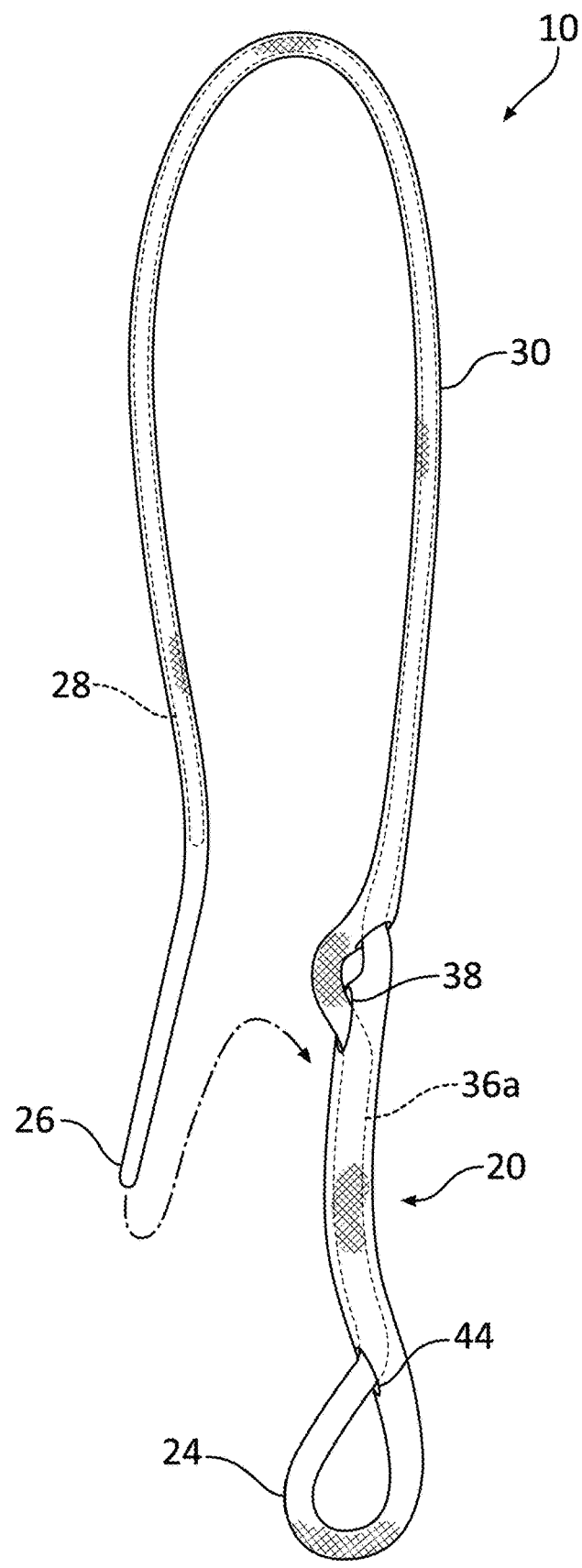
FIG. 23 illustrates an alternative embodiment of a multiple pass self-cinching suture construct positioned for insertion of a first tag end back through the self-cinching section in accordance with the present disclosure.
Figure 24:
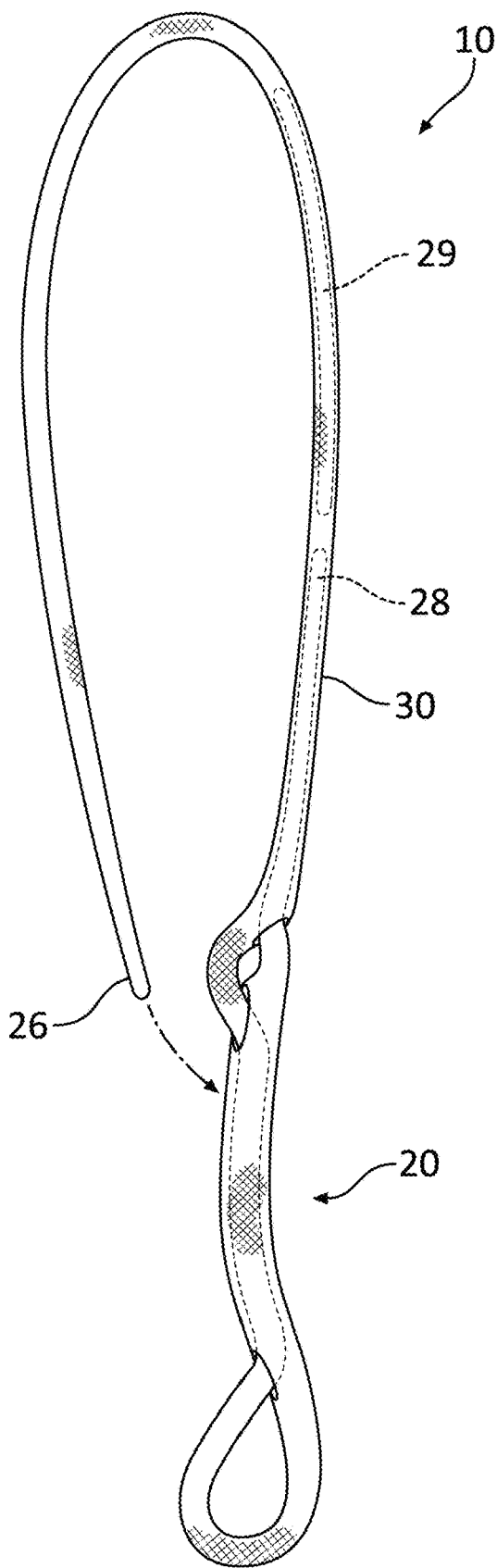
FIG. 24 illustrates an embodiment of a multiple-pass self-cinching suture construct in accordance with the present disclosure including a suture insert disposed in a first tag end to enhance grip of a self-cinching section.

Referring to FIG. 23, in some embodiments, suture construct 10 includes a second tag end 28 that extends in tag sleeve 30 a longer distance such that second tag end 28 approaches the distal end of first tag end 26. In such embodiments, when first tag end is inserted into self-cinching section 20 between first opening 44 and second opening 38 (and also enters into the interior axial passage of the section of suture material 36a housed inside self-cinching section 20), second tag end 28 housed inside tag sleeve 30 enters self-cinching section 20 earlier.

Referring to FIG. 29, in some embodiments, second tag end 28 terminates inside tag sleeve 30 on first tag end 26, and a separate suture insert 29 is disposed axially inside tag sleeve 30 on first tag end 26. Suture insert 29 may include an additional strand of suture material housed inside the hollow interior bore of first tag end 26. Suture insert 29 is positioned to be pulled into self-cinching section 20 when first tag end 26 is advanced through self-cinching section 20, and suture insert 29 is positioned axially inside first tag end 26 such that suture insert 29 will remain at least partially in the innermost axial position inside self-cinching section 20 when the suture construct 10 is fully tensioned. As such, suture insert 29 provides additional material inside first tag end 26 for self-cinching section 20 to clamp down against under tension, thereby enhancing the self-cinching function of self-cinching section 20 when the suture construct is tightened. Suture insert 29 can include any suitable flexible material for enhancing the gripping and constriction of self-cinching section 20 when tensioned, such as but not limited to a strand of suture material, braided suture material, hollow-core braided suture material, a polymer strand, a metal filament, a composite material, a woven material or other suitable materials. In some embodiments, the thickness or diameter of suture insert 29 may be adjusted to enhance the grip of self-cinching section 20 when suture construct 10 is fully tensioned. Suture insert 29 in some embodiments has a larger diameter than the suture material of suture construct 10. In other embodiments, suture insert 29 has a smaller diameter than the suture material of suture construct 10. In further embodiments, suture insert 29 has the same diameter as the suture material of suture construct 10.

Figure 25:
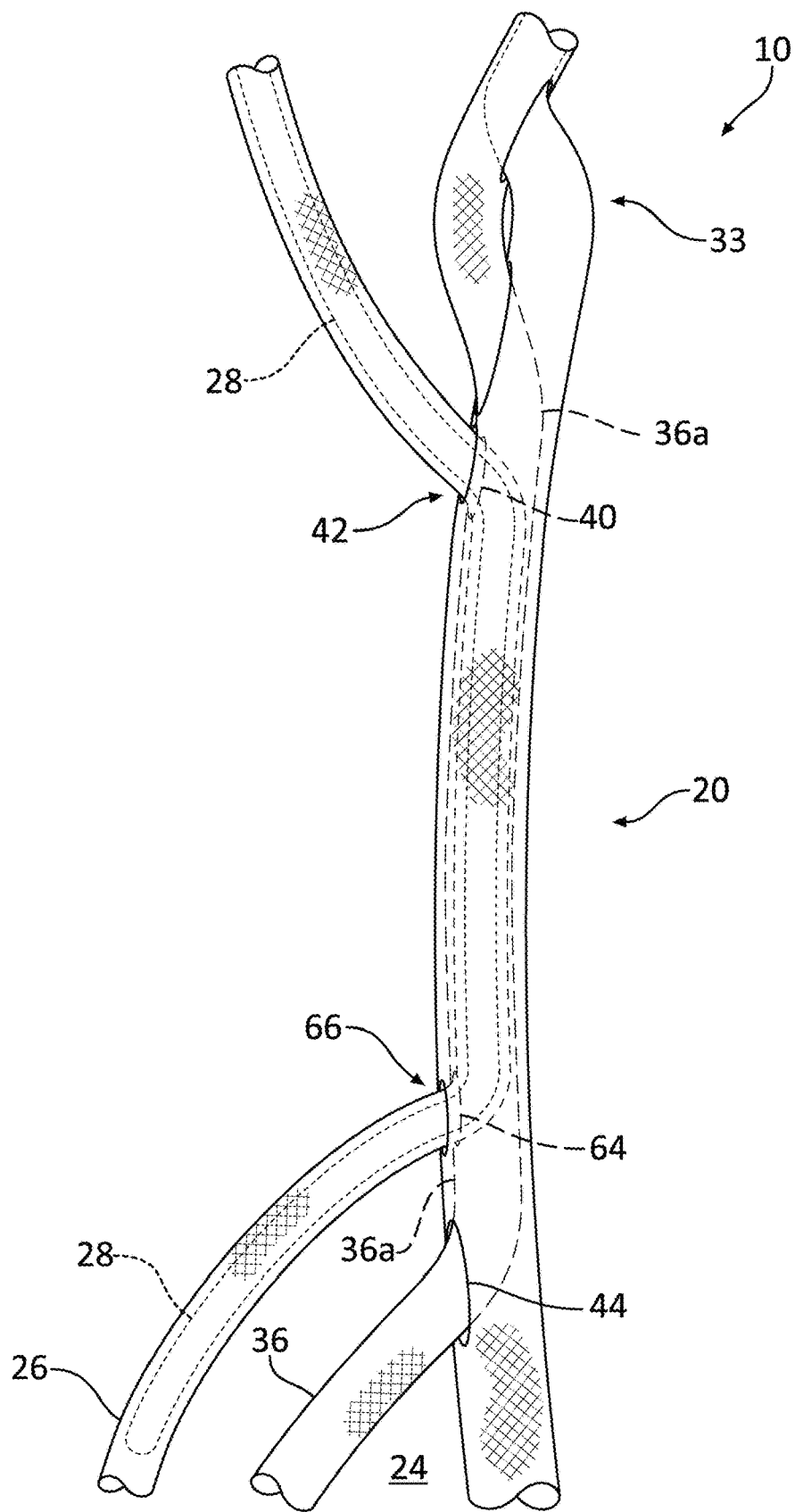
FIG. 25 illustrates a detail partial cross-sectional view of an embodiment of a self-cinching section of a multiple pass self-cinching suture construct including a first tag end (with a second tag end housed therein) passing through the self-cinching section and exiting along the self-cinching section in accordance with the present disclosure.

Referring to FIG. 25, in some embodiments, suture construct 10 includes a first tag end 26 that exits self-cinching section 20 between first opening 44 (where the section of fixed loop portion 36 enters) and fourth opening 42 (where the first tag end 26 entered self-cinching section 20). Such embodiments differ from the embodiment disclosed with respect to FIG. 5 because the first tag end 26 does not exit along a portion of fixed loop 24, but rather from an intermediate position along the axial length of self-cinching section 20. In such embodiments, a seventh opening 64 is defined in the portion of suture material 36a forming fixed loop housed inside self-cinching section 20. Additionally, an eighth opening 66 is defined in the outermost segment including a portion 20a of the main body of the self-cinching section 20 adjacent seventh opening 64. First tag end 26 exits self-cinching section 20 through seventh and eighth openings 64, 66 before reaching first opening 44. In such alternative embodiments, second tag end 28 housed axially inside first tag end 26 also exits self-cinching section via seventh and eighth openings 64, 66. This alternative embodiments provides a variation of the suture construct 10 in applications where it may not be desirable for first tag end 26 (with second tag end 28 housed axially inside) to exit along a portion of fixed loop 24.

Thus, although there have been described particular embodiments of the present invention of a new and useful MULTIPLE PASS SELF-CINCHING SUTURE CONSTRUCT, it is not intended that such references to particular embodiments be construed as limitations upon the scope of this invention except as set forth in the following Claims.

What is claimed is:

1. A suture construct apparatus, comprising:
   a suture strand including an adjustable loop at a first end and a fixed loop at a second end;
   a self-cinching section disposed on the suture strand between the adjustable loop and the fixed loop, the self-cinching section including first and second segments of the suture strand co-axially aligned;
   a first tag end of the suture strand extending axially inside both the first and second segments of the suture strand in the self-cinching section; and
   a second tag end of the suture strand housed axially inside a portion of the first tag end.

2. The apparatus of claim 1, wherein the second tag end housed axially inside a portion of the first tag end extends into and through the self-cinching section with the first tag end.

3. The apparatus of claim 2, wherein the first tag end exits a portion of the fixed loop between the second end and the self-cinching section.

4. The apparatus of claim 3, wherein the second tag end housed axially inside a portion of the first tag end exits the portion of the fixed loop between the second end and the self-cinching section with the first tag end when the suture construct is tightened.

5. The apparatus of claim 2, further comprising a shuttling suture disposed on the fixed loop.

6. The apparatus of claim 5, wherein a distal end of the first tag end is removably housed inside a portion of the shuttling suture.

7. The apparatus of claim 6, further comprising a continuous loop freely disposed on the adjustable loop.

8. The apparatus of claim 7, wherein the first tag end includes a progressive narrowing taper toward the distal end of first tag end.

9. The apparatus of claim 8, further comprising an anchor disposed on the fixed loop.

10. The apparatus of claim 9, wherein the anchor comprises a soft anchor.

11. The apparatus of claim 10, further comprising:
a shuttling suture loop disposed on an end of the shuttling suture, wherein the shuttling suture loop is disposed on the fixed loop.

12. The apparatus of claim 11, wherein the shuttling suture loop extends around the anchor on the fixed loop.

13. A suture construct apparatus, comprising:
a suture strand including an adjustable loop at a first end and a fixed loop at a second end opposite the first end; and
a self-cinching section disposed on the suture strand between the fixed loop and the adjustable loop,
wherein the self-cinching section includes two or more co-axially aligned segments of the suture strand extending axially inside the self-cinching section.

14. The apparatus of claim 13, further comprising a first tag end of the suture strand exiting the fixed loop between the second end and the self-cinching section.

15. The apparatus of claim 14, further comprising a first shuttling suture disposed on the fixed loop.

16. The apparatus of claim 15, further comprising a continuous loop freely disposed on the adjustable loop.

17. The apparatus of claim 16, further comprising a second shuttling suture disposed on the continuous loop.

18. The apparatus of claim 17, further comprising an anchor disposed on the fixed loop.

19. A suture construct apparatus, comprising:
a suture strand having a first tag end and a second tag end;
an adjustable loop formed by the first tag end;
a fixed loop formed by the second tag end; and
a self-cinching section on the suture strand between the fixed loop and the adjustable loop,
wherein a portion of the second tag end extends axially through the self-cinching section inside the suture strand toward the adjustable loop,
wherein the second tag end is housed in a portion of the first tag end passing through the self-cinching section toward the fixed loop, and
wherein at least two segments of the suture strand are co-axially aligned inside the self-cinching section of the suture strand.

20. The apparatus of claim 19, wherein the first tag end and the second tag end housed in a portion of the first tag end both exit the suture strand at a location on the fixed loop.

* * * * *